(12) United States Patent
Brown et al.

(10) Patent No.: US 7,161,059 B2
(45) Date of Patent: Jan. 9, 2007

(54) HUMAN HOOKWORM MODEL AND METHOD FOR MAINTAINING HUMAN HOOKWORM IN A NON-HUMAN PRIMATE

(75) Inventors: Alan Brown, Nottingham (GB); Doreen S W Hooi, Nottingham (GB); David Idris Pritchard, Nottingham (GB); Gareth David Griffiths, Wiltshire (GB); Peter Colin Pearce, Wiltshire (GB); Elizabeth Ann Marie Scott, Wiltshire (GB)

(73) Assignee: The Secretary of State for Defence in Her Britannic Majesty's Government of the United Kingdom of Great Britain and Northern Ireland, Salisbury (GB)

( * ) Notice: Subject to any disclaimer, the term of this patent is extended or adjusted under 35 U.S.C. 154(b) by 94 days.

(21) Appl. No.: 10/780,809

(22) Filed: Feb. 17, 2004

(65) Prior Publication Data

US 2004/0219105 A1 Nov. 4, 2004

(30) Foreign Application Priority Data

Feb. 15, 2003 (GB) ................. 0303691.0

(51) Int. Cl.
*A01K 67/00* (2006.01)
*A61K 49/00* (2006.01)

(52) U.S. Cl. ................. 800/9; 424/9.2; 800/8
(58) Field of Classification Search ............ None
See application file for complete search history.

(56) References Cited

OTHER PUBLICATIONS

Hotez, P.J., et al., "Experimental Approaches to the Development of a Recombinant Hookworm Vaccine", *Immunological Reviews 1999*, vol. 171, pp. 163-172 (1999).
Hotez, P.J., et al., "Vaccines for Hookworm Infection", *Pediatric Infectious Disease Journal*, vol. 16, No. 10, pp. 935-940 (1997).
Orihel, T.C., "*Necator americanus* Infection in Primates", *The Journal of Parasitology*, vol. 57, No. 1, pp. 117-121 (1971).
Orihel, T.C., "Primates as Models for Parasitological Research", *Medical Primatology Symp*. XXII, pp. 772-782 (1971).
Orihel, T.C., "The Helminth Parasites of Nonhuman Primates and Man", *Laboratory Animal Care*, vol. 20, No. 2, pp. 395-401 (1970).

*Primary Examiner*—Scott D. Priebe
(74) *Attorney, Agent, or Firm*—Kilpartrick Stockton LLP

(57) ABSTRACT

A method for maintaining a human hookworm strain is provided by infecting a non-human primate with a non-adapted or non-passaged human hookworm and maintaining the non-human primate. Methods of obtaining human hookworm materials and compositions, such as for use as a vaccine, are also provided, along with a model for maintaining and investigating human hookworm.

9 Claims, 6 Drawing Sheets

A

B

C

HUMAN HOOKWORM MODEL AND METHOD FOR MAINTAINING HUMAN HOOKWORM IN A NON-HUMAN PRIMATE

CROSS-REFERENCE TO RELATED APPLICATIONS

The present application claims the benefit of Great Britain Patent Application No. GB 0303691.0, filed Feb. 15, 2003.

FIELD OF THE INVENTION

This invention relates to a method of maintaining a live human hookworm strain and a related model for the development of vaccine candidates to protect against hookworm infection and other conditions.

BACKGROUND OF THE INVENTION

The development of vaccines for use as a treatment or prophylaxis against any one of a wide variety of different conditions is an extremely challenging scientific problem. In humans this is particularly challenging. However, because vaccines have been shown to be very successful at treating or preventing many types of conditions, there is an on-going need to identify new vaccine candidates, both to improve those vaccines currently on the market, but also to treat and protect against conditions for which no vaccine is currently available. One of the key tools required in the development of vaccines is a method of maintaining an on-going and authentic supply of the appropriate vaccine antigen formulation and also a model that can be used to understand immune responses, monitor disease progression or to test potential vaccine candidates. Preferably, such a method and model should exhibit both the complete patency and pathology of the condition following infection, and should also mimic the condition as closely as possible to that seen in a human host.

One particular disease for which there is a need to identify a vaccine candidate is the human hookworm infection, such as *Necator americanus* infection. It is currently estimated that a billion people worldwide harbour hookworm infections, making them a leading cause of anemia and malnutrition, particularly in children and women of child-bearing age in developing countries (Chan, M., et al., *Parasitology* 109:373–387 (1994); Hotez, P. J. and Pritchard, D. I., *Scientific American* 272(6):42–48 (1995); Stephenson, L., *Pathophysiology of Intestinal Nematodes* in *The Geohelminths. Ascaris, Trichuris* and Hookworm, C. V. Holland and M. W. Kennedy, Boston, *Kluwer Academic Press*, 2:39–61 (2001)). The infection is considered by many to represent a significant threat to the health and well being of afflicted communities and, consequently, efforts are being concentrated on developing a full understanding of the molecular biology of the host-pathogen interface, with a view to developing efficacious vaccines to protect against hookworm disease.

To this end, two major initiatives were recently announced, with the intention of increasing our knowledge of the molecular genetics of hookworms (The Wellcome Trust Beowulf Initiative) and to develop rationally designed vaccines for hookworm infection (The Hookworm Vaccine Initiative, Sabin Vaccine Institute and George Washington University). However, one of the major problems with these programs is that the hookworm lifecycle is difficult to maintain in animal models because of the subtle adaptation of the human hookworm to live in its definitive host. This also has the result that it is difficult to maintain an on-going supply of the hookworm larvae with the same molecular integrity as that which infects humans. As such, to support this work it is necessary to develop a method of maintaining a supply of human hookworms and also a vaccine model in animals that exhibits the full patency and pathology of human hookworm infection.

Several hookworm models are currently in existence, and these were developed to investigate the immunobiology of the human hookworm infection. These include the murine model of human hookworm infection, where an adult mouse is infected with the parasite. This model has several problems include the problem that the adult mouse is unable to retain adequate numbers of larvae in the gut. As a result, the model is unable to exhibit either the parasitology or the immunology of the human disease sufficiently accurately to be used as a mimic for the disease as exhibited in humans. The model cannot, therefore, be used for the development of either a vaccine or other medicaments.

In addition to the murine hookworm model, a canine model is also in use. Although this model is able to exhibit a form of the disease, the canine host is, unfortunately, unable to support human hookworm, and so the model utilises *Ancylostoma caninum*, the dog hookworm. While such a model is valuable for proof of principle studies, for example, with trial vaccines, it clearly has several limitations with respect to use as a model for studying human hookworm for the development of a human hookworm vaccine, because it utilizes a non-human hookworm species.

Finally, the hamster has been studied for use in work of this type. It has been shown that it is not possible to infect an adult hamster with anthropomorphic strains of the parasite which causes the disease, and, therefore, this species cannot be used as a model as such, whereby, for example, the animal is pre-vaccinated prior to challenge, etc. A further problem also exists in that the model does not respond to L3 larvae, again, because of the inability to use adult animals. However, the hamster has proved to be a valuable tool for the maintenance of a hookworm strain in the laboratory. The neonate is infected with the hookworm larvae; the hookworm is passaged through the animal, collected, and then either used for experimental purposes, or re-passaged to maintain further supplies. Hookworms obtained in this manner have proved useful for further understanding the protective inflammatory responses to hookworm challenge following vaccination (Ghosh, K. and Hotez, P., *The Journal of Infectious Diseases* 180:1674–1681 (1999); Hotez, P. J., et al., *Immunological Reviews*, 171:163–172 (1999); Liu, S., et al., *Vaccine*, 18:1096–1102 (2000); Culley, F. J., et al., *European Journal of Immunology*, 32(5):1376–1385 (2002)). However, recently it has been shown that hookworm passaged in this manner does not remain true to the authentic strain of human hookworm. Hence, there are several limitations when trying to utilise such material as part of a model for human hookworm, for example, for development of a vaccine, or other medicaments.

As such, to date, there are several problems associated with the known animal models for development of human hookworm vaccines, and it is, therefore, desirable to develop a well characterised primate model to enable the future vaccine development in a species closely allied to man (*Homo sapiens*). Such a model has several advantages, including that it is able to support the human hookworm infection throughout the whole life cycle, it provides an on-going source of authentic hookworm causative agent, it provides a more effective mimic for the immunological response of a human to the hookworm infection, and, therefore, provides a greater understanding of its pathology, and also provides a better vehicle for monitoring the efficacy of any vaccine candidates. The model and associated methods are used to provide materials required during the development program, test the efficacy and toxicity of desirable vaccine candidates, assess adjuvants, delivery routes and systems, frequency of inoculation, and to ascertain the immunological phenotype associated with protection with a higher degree of experimental validity than is available to date with known hookworm models.

SUMMARY

A method of maintaining human hookworm has now been developed. The method utilizes a primate host. This method has been developed to provide a hookworm model that overcomes the problems mentioned above. In accordance with the method, a non-human primate is infected with a human hookworm. Preferably, the primate is a marmoset, and, more preferably, *Callithrix jacchus*. The hookworm is a non-adapted or non-passaged human hookworm, preferably a fresh human hookworm isolate. For example, the hookworm described herein was a field isolate collected in October, 2001, from Papua New Guinea (Haven, Madang Province). The method has demonstrated for the first time that, unexpectedly, immunogenic patent and pathological infections can be established in a primate. By use of this method a model has been established which demonstrates the patency of the human hookworm infection when infected with fresh field isolate of *Necator americanus* obtained from an infected human. This is the first time that a model is provided which is authentically able to mimic a hookworm infection in a human.

Significantly, data obtained from the models described herein indicated that the pathology of the disease was much more severe in primates infected with fresh field isolate than in those animals infected with hamster-adapted hookworm strain. In animals infected with fresh field isolate, the hemoglobin levels, packed cell volume, and erythrocyte counts were significantly reduced, while those infected with the laboratory strain showed no evidence of this pathology. This indicates that attenuation had likely occurred in the hamster adapted laboratory strain, presumably as a result of repeated passage through hamsters, as this strain has been maintained since 1983. These results further demonstrate that the hamster-adapted laboratory strain of human hookworm has several restrictions when used as a mimic for human hookworm infection, and is unlikely to be useful as an effective source of hookworm infection for use in a model to assess vaccine candidates. As such, development work conducted using hamster source of hookworm infection is likely to be flawed.

Interestingly, one animal infected previously with the laboratory strain, and subsequently infected with the field isolate, may have been protected from pathology by the attenuated laboratory strain. Further assessment of the infection showed it to be associated with increased total plasma immunoglobulin E (IgE) levels and the appearance of specific immunoglobulin G (IgG) antibodies to adult worm excretory/secretory (ES) products. This was demonstrated by using enzyme-linked immunosorbent assay (ELISA) and Western blotting techniques in conjunction with a panel of well characterised anti-human reagents. The appearance of antibodies seemed not to be affected by the type of hookworm infection used, and, in both cases, the immune response was reminiscent of that seen in infected patients in endemic areas. Finally, whole blood basophil histamine release was recorded to anti-IgE, ES products, and a recombinant hookworm allergen, calreticulin, again, in parallel with observations made in human populations. The basophil histamine release to multiple agonists was found to be most consistent in animals exposed to the field isolate, likely reflecting more efficient loading of $Fc_{\epsilon}RI$, a high affinity receptor for immunoglobulin E, on basophiles with parasite-specific IgE, which was not detectable serologically due to the low sensitivity of anti-human IgE reagents in ELISA. Again, these results demonstrate the limitations of the conventional hamster-adapted laboratory strain of hookworm infection and the advantages of the model provided herein.

It is believed that this method provides for the first time a mechanism for maintaining human hookworm infection with the integrity of a fresh field isolate. It is believed that the associated primate model provides, for the first time, a unique opportunity to accelerate the development of a hookworm vaccine in a system, where vaccine safety, delivery and efficacy can be assessed against worm establishment, parasite patency, infection-associated pathology and immunological characteristics associated with the human hookworm infection. The infection of primates with fresh field isolates of *Necator americanus* also provides an adequate and informative tertiary model for the assessment of adjuvant safety in that the model offers many of the pathological and immunological features associated with hookworm infection of the definitive host. It is also believed that this model provides, for the first time, an opportunity to dissect immunologically and physiologically the relationship between parasitic infection and the development of allergenic sensitivity to environmental allergens, thus accelerating work to establish any relationship between the apparent protective effects of hookworm infection against the development of respiratory allergies to dust mites.

It is an object of the present invention to develop a model for the use in the development of hookworm vaccines. It is a further object of this invention to develop a primate model that is able to exhibit the patency and pathology of a human hookworm. It is another object of this invention to develop a model that can accelerate the development of a human hookworm vaccine. These and other objects of this invention will become apparent in light of the following disclosure.

According to one aspect, this invention relates to a method of maintaining human hookworm by infecting a non-human primate with human hookworm and maintaining the non-human primate.

According to another aspect, this invention relates to a method of obtaining human hookworm larvae by maintaining the hookworm according to the method described herein and retrieving the hookworm larvae from the fecal material of the non-human primate.

According to a further aspect, this invention relates to a composition containing human hookworm material, obtained by a process involving obtaining human hookworm larvae, maintaining the hookworm according to the method described herein and retrieving the hookworm larvae from the fecal material of the non-human primate.

According to yet one more aspect, this invention relates to a method of developing a therapeutic agent by utilizing human hookworm obtained according to the method described herein.

According to still one more aspect, this invention relates to a model for investigating human hookworm, wherein the model is a non-human primate infected with a human hookworm isolate. This invention also relates to the use of such a model.

DETAILED DESCRIPTION OF THE INVENTION

Figure 1:
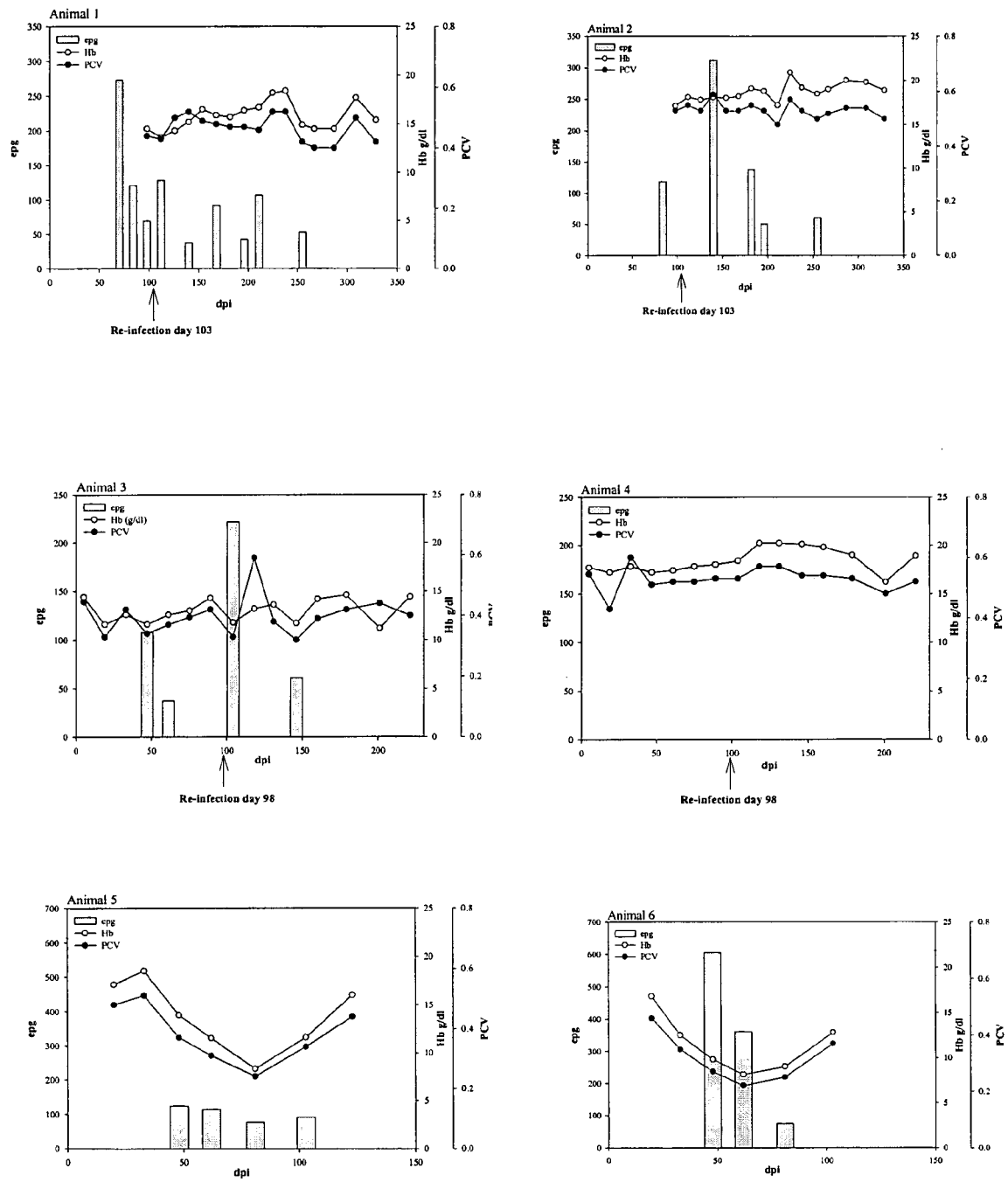
FIG. 1 are the plots showing the egg production, hemoglobin levels and packed cell volume of each different primate over time.

A method of maintaining a human hookworm and a human hookworm model are provided herein. In accordance with the method, a primate is infected with a human hookworm and the primate maintained. The preferred primate is a marmoset, more preferably *Callithrix jacchus*, and the hookworm is a non-adapted, or non-passaged, human hookworm, preferably a fresh human hookworm isolate, or field isolate. The model is authentically able to mimic hookworm infection in a human. The elements of the aspects and preferred embodiments of the present invention, including the method and model and methods of using both, are described in more detail below.

General Terms and Definitions

The terms "a", "an" and "the" as used herein are defined to mean "one or more" and include the plural unless the context is inappropriate.

As used herein, the phrase "therapeutic agent" is any agent for use to treat a disease or a condition in an animal, including a human.

As used herein, the terms "develop" or "developing" in reference to a model or a therapeutic agent, are generally used in the disclosure of the preferred embodiments of the present invention to denote processes, methods, and procedures involved in or associated with discovering a model or a therapeutic agent, and establishing its properties, including therapeutic effectiveness.

As used herein, the term "obtain", particularly in reference to hookworm materials, is used to denote the action of gaining or attaining, including gaining or attaining by planned action or effort, and is, in the disclosure of certain preferred embodiments of the present invention, used interchangeably with the term "retrieve."

As used herein, the term "infection" or "active infection," and derivatives thereof, particularly in reference to hookworm infection, is used herein to denote one or more of: the act or result of affecting injuriously by an infective agent; such as a bacterium, a virus, or a parasite; an infective agent or material contaminated with an infective agent; the state produced by the establishment of an infective agent in or on a suitable host, such as an animal or a human; a disease, a condition, or any biological responses resulting from infection; an act or process of infecting; and the establishment of a pathogen in its host after invasion.

As used herein, the term "model" in reference to a model of infection, includes an animal model for investigation of a human infection, and is used in the preferred embodiments of the present invention to denote an animal that has a disease, a condition, or an infection similar to that in ethiology or pathology to a human disease, a condition, or an infection. The disease, condition, or infection can be purposefully induced in the animal model. The animal model is used to study the way the disease progresses and what factors are important to the disease process. The animal model can also be used to study disease treatment, which can be done through the use of controlled experiments.

As used herein, the term "primate" denotes all living primates, including the two great groups, the *Stepsirhini* and the *Haplorhini*, wherein the *Strepsirhines* include mostly arboreal species with many primitive characteristics, but at the same time, some extreme specializations for particular modes of life, and wherein the *Haplorhines* are the so-called "higher" primates, further divided into two major groups, the *Platyrrhini* and the *Catarrhini*. The *Platyrrhines* have flat noses, outwardly directed nasal openings, three premolars in upper and lower jaws, anterior upper molars with three or four major cusps, and include two genera that fall under the category of marmosets, *Callithrix* and *Cebuella*, and include a total of eight known species of marmosets, including, in the *Callithrix* genus: Tassel-ear marmoset (*C. humeralifer*); Bare-ear marmoset (*C. argentata*); Common marmoset (*C. jacchus*); Black tufted-ear marmoset (*C. penicillata*), Buffy tufted-ear marmoset (*C. aurita*); Geoffroy's tufted-ear marmoset (*C. geoffroyi*); Buffy-headed marmoset (*C. flaviceps*); and, in the *Cebuella* genus, Pygmy marmoset (*C. pygmaea*). The *Catarrhines* have paired, downwardly directed nasal openings, which are close together; usually two premolars in each jaw, anterior upper molars with four cusps, and include, but are not limited to, *Cercopithecidae, Hylobatidae*, and *Hominidae*, including *Homo sapiens*. Most primate species live in the tropics or subtropics, although a few, most notably humans, also inhabit temperate regions. Except for a few terrestrial species, primates are arboreal. Some species eat leaves or fruit; others are insectivorous or carnivorous. It is to be understood that the foregoing classification is non-limiting and includes past, present, and future variations and changes as known to those skilled in the art.

As used herein, the term "vaccine" denotes a composition containing an immunogenic agent that is administered to produce or artificially increase immunity to the immunogenic agent.

Hookworm

For the purposes of the present application, the term "human hookworm" is any human hookworm of class *Secernentea*, order *Strongylida*, also known as *Strongylata*, superfamily *Ancylostomatoidea*, and families *Ancylostomatidae, Ancylostomidae*, or *Uncinariidae*, including, but not limited to, the major species *Necator americanus* and *Ancylostoma duodenale*. It is to be understood that all species of the human hookworm fall within the scope of the embodiments of the present invention.

In nature, the lifecycle of the hookworm described herein is as follows. Eggs are passed with the feces. Eggs hatch in about 48 hours under favorable conditions: (a) moist aerated soil; (b) protection from direct sun rays; (c) temperature of about 25° C. Excess water, high soil acidity, direct sunlight and drying inhibit hatching. The first-stage juveniles feed upon bacteria in the feces for about three days and then molt to second-stage juveniles. First and second stage juveniles have a rhabditiform esophagus. A second molt occurs in five to eight days and these juveniles are the third-stage infective juveniles, they do not feed, and may retain the cuticle of the second-stage juveniles which provides some protection from adverse environmental conditions, and have a strongyliform esophagus (posterior bulb not separated from the corpus by an isthmus). The are able to survive six to nine weeks at 25° C. and four weeks at 15° C. At 0° C., death occurs rapidly. The infective juveniles move to the surface of the soil and wave back and forth, which increases the chance to contact a host.

Infection by human hookworm is through the skin (percutaneous), usually the feet or hands. After penetration, the juveniles are carried by venous blood to the heart, to the lungs, break through into air sacs, to the trachea, and upon being swallowed pass to the small intestine. Here they attach to the intestinal mucosa or villi where they feed on blood, and molt twice to adults. Copulation takes place and eggs appear in the feces about 6 weeks after infection. Approximately five weeks pass from infection to the production of eggs. Adult worms may live five years or more but most live for short periods. Peak egg production is reached about six months after infection. The number of eggs laid by individual females varies with the number of worms present but may reach 5–10,000 in light infections. A female may lay several thousand eggs per day.

In the present application, the term "hookworm larvae" is used interchangeably with the term "hookworm juveniles" and is used to denote any stage of hookworm juveniles as disclosed herein, particularly hookworm juveniles that are infective, or capable of causing a hookworm infection in an animal or a human. It is also to be understood that, in the present application, the term "hookworm" is used to denote any stage of the hookworm lifecycle, including, but not limited to, adult hookworms, juveniles, and eggs.

The human hookworm used in certain aspects or embodiments of the present invention can be initially obtained from a wide variety of different sources. Preferably, the hookworm is a non-adapted human hookworm, including, but not limited to, a hookworm obtained from a reliable source of a non-passaged human hookworm, or, more preferably, the hookworm is a fresh human hookworm isolate. The term "non-adapted," when used in reference to a human hookworm, denotes the hookworm that maintains the characteristics, such as, but not limited to, patency, pathology and immunological characteristics, similar to that exhibited by the human hookworm in a human host. The term "non-passaged," when used in reference to a human hookworm, denotes the human hookworm that inhabited a human host at least during the host-based part of the lifecycle directly preceding infecting a non-human primate according to certain embodiments of the present invention. The term "human hookworm isolate" or "field isolate" are used here to denote hookworm obtained or derived from an infected human. Prior to infecting a non-human primate according to certain embodiments of the present, both non-passaged human hookworm and fresh human hookworm isolate are maintained without a host in laboratory conditions for at least a part of their lifecycle.

The human hookworm isolate used as described herein was obtained from a fresh *N. americanus* isolate from an infected human. In this instance, fecal material was obtained from a hookworm-infected individual living in Haven village on the Bogia Coast Road, Madang Province in October, 2001, and was cultured as previously described (Harada, Y. and Mori, O., *Yonago Acta Medica,* 1:177–179 (1955)). Freshly cultured larvae were used to infect marmosets (Dstl, Proton Down, UK). As a control, this larvae was also used to infect neonate hamsters (University of Nottingham, UK).

In accordance with the method described herein, a non-human primate is infected with the human hookworm infection. Preferably, the primate used is a marmoset, more preferably, *Callithrix jacchus*. Common marmosets (three male and three female, bred at CBD Porton Down) weighing 319–516 g were used. These were maintained as mixed sex pairs, where the males had been vasectomized. Each pair of primates were housed in four stainless steel cage units measuring H 72×W 47×D 60 cm connected together by two horizontal external extensions and one vertical extension (H 18×W 71×D 23 cm and H 105×W 17×D 23 cm, respectively) in order to allow full use of all four units. The cages comprised various items of cage furniture, including hanging wooden dowels, buckets and other playthings, which were also placed in the cages. Illumination was provided by sodium lighting, at a level of 350–400 lux, 1 m from the ground, using a 12 hour light/dark cycle with dusk and dawn effects over 1 hour periods. The primates were maintained on a daily diet of 20 g pellets (SDS primate diet (Special Diet Services (SDS), Withams, Essex, UK), CPDE) with supplements of orange segments. Additional supplements included banana, apple and egg. The primates were additionally fed from a tray hanging below a horizontal extension on their cage, which was filled with sawdust in which a small amount of preferred foods, such as raisins, was dispersed such that the primates engage in foraging behaviour. Water was available ad libitum. During behavioural training and testing, the pairs were separated so that each had use of a single upper unit of its home cage with a rigid extension unit (H 18×W 17×D 30 cm) attached to the front.

The primates were infected with the hookworm isolate, preferably using a transcutaneous route of administration, or infection. In one method, marmosets were anaesthetised with ketamine (15 mg per animal) and an area of skin approximately 2 cm$^2$ just below the scapula, shaved. Infective larvae were placed on a gauze fixed to a self adhesive horse bandage (International Market Supply, Dane Mill, Broadhurst Lane, Congleton, Cheshire, CW12 1LA). The bandage was subsequently wrapped around the thorax and held in place with a tubigrip jacket. The jacket and bandage were removed after 24 hours. The primates were infected with from about 200 to about 1000 larvae, respectively.

The infected primates were maintained under study for a period of three to twelve months following infection. During this time primates were routinely observed to ensure that they were taking food and water. They were also observed in case of the occurrence of any specific adverse signs, for example, lethargy or problems of a respiratory nature following infection, and the like. Blood samples were taken twice monthly in order to monitor specific antibody formation, red blood cell count, haemoglobin level and packed cell volume. These were used both as a source of information regarding the progress of the infection and also, as the infection progressed, to ensure that the animals were not in danger of adverse side effects due to blood loss. All blood samples were taken in accordance with recommended animal welfare guidelines ("Removal of blood from laboratory mammals and birds," *Laboratory Animals* (1993) 27:1–22).

Method of Obtaining Human Hookworm Larvae

Also provided herein is a method of obtaining human hookworm larvae by maintaining the hookworm according to the method described above and retrieving the hookworm larvae from the fecal material of the primate using standard isolation techniques for example as described in Carr A. and Pritchard D. I., *Parasite Immunology*, 9:219–234 (1987). Human hookworm obtained in this manner can have many uses. For example this method is used to provide an on-going sustainable source of human hookworm which maintains the patency, pathology and immunological characteristics of human hookworm in a human host.

The term "patency" as used herein is known to one skilled in the art and, in reference to parasitic worm infections, is generally used to denote a period of egg larvae production by the parasitic worm (for a non-limiting example, see Arneberg, P., el al., "Parasite Abundance, Body Size, Life Histories, and the Energetic Equivalence Rule", *The American Naturalist*, 151:497–513 (1998)). The term "pathology" is used herein in reference to a parasitic worm infection to describe changes in a host organism associated with the parasitic worm infection, including, but not limited to, structural, functional, biochemical, or histological change.

Human hookworm obtained according to certain embodiments of the present invention is used in a method to develop a therapeutic or prophylactic agent by any one of standard developmental techniques known to one skilled in the art. A specific example of a therapeutic or prophylactic agent that such hookworm is used to develop is a vaccine, more preferably a human hookworm vaccine. Such a development method provides several advantages over known development methods utilising known neonate adapted hookworm, because the hookworm infection according to the preferred embodiments of the present invention exhibits the patency, pathology and immunology of human hookworm.

Hookworm Model

A model for investigating human hookworm is provided, wherein the model is a non-human primate infected with a human hookworm isolate. In particular, this model exhibits the patency, pathology and immunology of the hookworm infection essentially as that exhibited in a human host. This model provides several advantages over hookworm models already known. These include, but are not limited to, the advantage that the hookworm is a wholly representative model of human hookworm in a human host, because it utilizes a host that is known to be very similar to a human and that has been infected with the human hookworm itself. In addition, due to the similarities between the non-human primate and the human, the rate of the adaptation of the human hookworm, if at all, will be much slower in a non-human primate host than in a murine host. This has the effect that the human hookworm retains the same integrity as displayed in a human host for a much longer period of time. Such a model has many uses in the scientific areas of developing an understanding of the hookworm infection, and in developing new methods of treatment and prevention of the hookworm infection and related conditions. Examples of specific and important uses of such a model include, but are not limited to, development of a hookworm vaccine, investigation into the immunological response to human hookworm, development of a greater understanding of the relationship between the hookworm and allergenic sensitivity to environmental allergens, and development of a vaccine for protection against the development of respiratory conditions.

Methods and Compositions for Inducing an Immune Response to Human Hookworm

Also provided herein is a method of inducing an immune response to a human hookworm pathogen by administering an antigenic hookworm material to a human or an animal in a sufficient amount to induce an immune response. The hookworm material includes, but is not limited to, hookworm larvae or human hookworm, or fragments, or components thereof, including but not limited nucleic acids, lipids, carbohydrates, or proteins thereof, or any combination thereof, obtained from the hookworm model described herein. The hookworm material is combined with excipients or carriers to form an antigenic hookworm composition or vaccine. Upon induction of an immune response, the human or animal develops at least partial resistance or immunity to subsequent infection with pathogenic or infectious human hookworm.

When used to induce a protective or therapeutic immune response, such as during the use as a vaccine, non-pathogenic hookworm material can be used. The hookworm material can be inactivated prior to administration by being killed or attenuated so that pathogenic infection is avoided.

Also provided herein is a method of treating a human hookworm infection in a human or an animal, by administering to the human or the animal the non-pathogenic hookworm material or composition in a sufficient amount to induce an immune response. The human hookworm material is preferably combined with a pharmaceutically acceptable carrier to facilitate administration.

The preferred dose for administration of the hookworm material or composition to the human or the animal is adjusted to suit the human or the animal to whom the composition is administered, and the purposes of a particular method during which the human hookworm is administered, and varies with certain factors such as health, age, weight and metabolism of the human or the animal, and is, for example, 0.1 to 1000 of infectious doses per the human or the animal, or 1 to 100 infections doses, or 1 to 10 infectious doses. An infectious dose may include one or more hookworm larvae, for example, up to 10,000 larvae, or up to 1,000 larvae, or between about 100 to between about 1000 larvae, or between about 300 to between about 1000 larvae. Alternatively, a preferred dose for administration is expressed in weight of the hookworm material per weight of the person, and is, for example, 0.001 mg/kg to 10 mg/kg. The hookworm material, prior to administration, may be combined with stabilizers or physiologically acceptable preservatives.

The hookworm material and composition containing the hookworm material is administered by any appropriate route, including but not limited to, percutaneously, transcutaneously or transdermally, including, but not limited to, administering live hookworm larvae to an area of a skin of a human or an animal, or providing access to live hookworm larvae to the area of the skin of the human or the animal, orally (e.g. buccally or sublingually), rectally, as a suppository or an enema, topically, parenterally, subcutaneously sub-dermally intramuscularly, intraperitoneally intravesicularly, intraarticularly, intravenously, intradermally, intracranially, intralesionally, intrathecally, intratumorally, intraocularly, ocularly, aerosolically, intrapulmonaryly, intraspinally, intraprostaticaly, sublingually, or by placement within cavities of the body, nasal inhalation, pulmonary inhalation, impression into the skin and electroporation, intrauterinaly, vaginally, into a body cavity, surgically administered, or administered into the lumen or parenchyma of an organ, and into bone marrow. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a joint capsule, or elsewhere.

The hookworm compositions described herein can be applied in the form of creams, gels, solutions, suspensions, liposomes, particles, or other means known to one of skill in the art of formulation and delivery of compositions. Ultrafine particle sizes can be used for inhalation delivery of therapeutics. Some examples of appropriate formulations for subcutaneous administration include but are not limited to implants, depot, needles, capsules, and osmotic pumps. Some examples of appropriate formulations for transdermal and transmucosal administration include but are not limited to creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

The compositions may conveniently be presented in unit dosage form and may be prepared by conventional pharmaceutical techniques. Such techniques include the step of bringing into association the compositions containing the active ingredient and the pharmaceutical carrier(s) or excipient(s), in liquid or solid form, in a single dose or a dose repeated after a certain time interval. The hookworm material may also be provided in a lyophilized form, reconstituted in an appropriate solvent such as deionized water or saline and administered as a single dose or a series of doses at a time intervals necessary for the achievement of the desired response, including, but not limited to, a hookworm infection or an immunological response.

For the purposes of the present invention, immunological response, or a human hookworm infection in a primate, or both, is characterized by or associated with changes in one or more of, but not limited to, the foregoing: increased total plasma immunoglobulin E (IgE) levels; appearance of specific immunoglobulin G (IgG) antibodies to the hookworm material, including, but not limited to, to adult worm excretory/secretory (ES) products, and as detected by a variety of methods known to one skilled in the art, such as, but not limited to, enzyme-linked immunosorbent assay (ELISA) or Western blotting techniques; whole blood basophil histamine release to anti IgE, or ES products, or any naturally occurring or recombinant hookworm allergen, such as calreticulin; more efficient loading of FceRI, a high affinity receptor for immunoglobulin E, on basophiles with parasite-specific IgE; red blood cell count, haemoglobin levels, or packed cell volume.

In one preferred embodiment, the administration of human hookworm material to a human or an animal results in induction in the human or the animal of an active hookworm infection, including, but not limited to, patency, pathology, or immunology characteristic of the active human hookworm infection. In a variation on a preferred embodiment, the administration of the hookworm material to the human or the animal results in acquisition by the host of immunity against the hookworm infection, including, but not limited to, active or passive immunity as known to the persons skilled in the art.

In another preferred embodiment, the administration of human hookworm material affects, alters, modulates, or modifies allergic responses, including allergies or allergenic sensitivity, to a variety of environmental factors, or agents, found in the environment, including, but not limited to, responses, such as respiratory wheeze or allergy, to dust mites. A probability appearance or manifestation of the allergenic responses in a human or an animal can also be affected, altered, modulated or modified.

This invention is further illustrated with reference to the following experiments, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Experiments

In order to ascertain the success of the methods and models disclosed herein, several experiments were conducted to compare the hookworm obtained by the method described herein, i.e. from marmosets infected with human hookworm isolate, with a hookworm obtained from a control model, and with marmosets infected with hamster adapted strain of human hookworm, i.e. the hookworm strain typically used in laboratories today.

The control primates were infected with hamster adapted laboratory strain of *Necator americanus*. The strain was originally obtained in 1983 from Dr. G. Rajasekariah of Hindustan, CIBA-GEIGY Ltd., Bombay, India and has been maintained in syngeneic DSN hamsters (*Mesocricetus aureus*) at the University of Nottingham since that date (Pritchard D. I., et al., *Parasite Immunology* 8:359–367 (1986)). The laboratory strain has been maintained as follows. Two to four (2–4) day old neonate hamsters are infected percutaneously with 100 infective third stage larvae and the infection allowed to proceed until adult worms in the small intestine became fecund approximately 42 days post-infection. To obtain fresh infective larvae, fecal material containing *N. americanus* eggs are cultured by a method described by Kumar, S. and Pritchard, D. I., *International Journal For Parasitology* 22(5):563–572 (1992). Fecal material is mixed with activated charcoal, 1% (w/v) amphotericin B (final concentration) and water to form a smooth paste, which is applied to the upper half of a 5×30 cm strip of filter paper. The strips are then suspended in a large glass chromatography tank containing approximately 750 ml of distilled water. The tanks are sealed and incubated at 28° C. for 7–10 days, after which the filter paper strips carefully removed and discarded. The water containing the larvae is transferred to a measuring cylinder and the larvae allowed to settle for two hours. After this period, the water is aspirated off and the larvae washed twice to remove any fecal contamination. Finally, washed larvae are re-suspended and stored in distilled water until required. The strain used in these experiments has been passaged approximately 460 times through DSN hamsters since the time that it was initially obtained from Ciba Geigy in 1983. The control primates were infected with the hamster adapted laboratory strain of *Necator americanus* as described above.

The primates were infected as follows: Primates 1 and 2 were infected with 300 laboratory strain larvae and re-infected with 300 laboratory strain larvae on day 103. Primate 3 was infected with 300 laboratory strain larvae and re-infected with 300 laboratory strain larvae on day 98. Primate 4 was infected with 300 laboratory strain larvae and re-infected with 300 human strain larvae on day 98. Animals 5 and 6 were infected with 300 and 600 human strain larvae respectively.

The following were monitored in order to assess the primate model: egg production, which was assessed using salt floatation (Keymer A. E. et al., *Parasitology* 101: 69–73 (1990)); haemoglobin levels (normal range 14.9–17.9 g/dl), erythrocytes (normal range $5.7–6.95 \times 10^{12}$/l), and mean erythrocyte cell volume (MCV, normal range 48–87 fl) were measured using a Baker 9000 haematology analyser; packed cell volume was measured using a Hawksley hematocrit centrifuge and reader (normal range 0.42–0.52); peripheral blood leucocytes were measured using a Baker 9000 haematology analyser (normal range $7.3 \times 10^9$/l).

Further studies were also conducted to assess the human hookworm infection compared to that of the control hamster adapted laboratory strain.

Adult *N. americanus* excretory/secretory (ES) products were collected as described by Brown, A. and Pritchard, D. I., *Parasite Immunology*, 15:195–203 (1993). *N. americanus* infected hamsters were killed 35 days post-infection and the small intestine removed, cut along its length, and placed in a petri dish containing Hanks buffered saline solution (HBSS). The petri dishes were incubated at 37° C. to allow the adult worms to detach voluntarily from the intestine thus minimising the possibility of host tissue contaminating subsequent ES cultures. Detached adult worms were washed extensively in RPMI 1640 containing 100 i.u./ml penicillin and 100 μg/ml streptomycin over a period of 2 h followed by further culture in RPMI 1640 for 24 h. ES products obtained after 24 hours were stored at −20° C. until required.

The proteolytic activity of normal and heat inactivated ES products was determined using fluorescein isothiocyanate labelled casein (FITC-casein) as described by Beynon R. J. and Bond, J. S., *Proteolytic enzymes-a practical approach*, Oxford, IRL Press, 1989. Twelve (12) μg of ES (20 μl) products were mixed with 10 μl of FITC-casein (stock 0.5 mg/ml) and 170 μl of 50 mM phosphate buffer, pH 6.5, containing 5 mM cysteine and incubated at 37° C. for 2 h. To stop the reaction and precipitate any undigested protein, 120 μl of 5% w/v trichloroacetic acid was added and the tubes allowed to stand at room temperature for 1 hour. Precipitated protein was removed by centrifugation at 13,000 g for 10 minutes. Triplicate, 20 μl aliquots of the supernatant were added to 80 μl of 0.5 M Tris, pH 8.5, and the fluorescence measured (excitation 490 nm, emission detection 525 nm) using a Dynex MFX microplate fluorimeter.

The expression and purification of recombinant calreticulin was conducted as follows. *E. coli* M15 (pREP4) transformed with the plasmid pQE-CalΔSig, which encodes *N. americanus* calreticulin deleted by PCR of the N-terminal signal sequence and fused to 6x histidine tag to facilitate affinity purification (Pritchard, D. I., et al. *Parasite Immunology*, 21: 439–450 (1999)) were grown overnight at 37° C. in LB broth containing kanamycin (30 μg/ml) and ampicillin (200 μg/ml). The culture was diluted 1:7 in fresh medium and, after 30 min, IPTG was added to a final concentration of 2.8 mM. After vigorous shaking for 3 hours at 37° C., the culture was harvested by centrifugation.

Recombinant calreticulin was purified using a combination of 'Bugbuster' protein extraction reagent (Novagen, EMD Biosciences, Inc., San Diego, Calif.) and a His Bind Purification kit (Novagen). Harvested cells were resuspended in Bugbuster reagent (5 ml per gram of cell pellet) containing 25 units benzonase per ml of Bugbuster reagent and incubated at room temperature for 20 min. Insoluble cell debris was removed by centrifugation at 16000 g for 20 min at 4° C. and the supernatant loaded directly onto a 5 ml His bind resin column previously equilibrated with 5 column volumes of 50 mM $NiSO_4$ followed by 3 column volumes of binding buffer (5 mM imidazole, 0.5 M NaCl, 20 mM Tris-Cl, pH 7.9). Following application, the column was washed with 10 volumes of binding buffer and 6 volumes of wash buffer (60 mM imidazole, 0.5 M NaCl, 20 mM Tris-Cl, pH7.9) prior to elution. Bound calreticulin was eluted with 6 column volumes of elute buffer (1 M imidazole, 0.5 M NaCl, 20 mM Tris-Cl, pH 7.9). Fractions containing calreticulin as determined by protein estimation (Bio-Rad Laboratories, Inc., Hercules, Calif.) were pooled, dialysed against PBS and stored at −20° C. until required. The purified recombinant protein was sequenced by MALDI-TOF mass spectrometry to confirm its identity.

The immunology was investigated by determining both the total IgE response and the specific IgG response in each of the primates. The total IgE response was determined by coating a 96 well polystyrene plate with 50 μl of a mouse anti-human IgE (BD Biosciences Pharmingen, San Diego, Calif.), 5 μg/ml diluted in 0.05 M carbonate/bicarbonate buffer, pH 9.6, overnight at 4° C. The plates were washed with phosphate buffered saline/0.05% Tween 20, pH 7.2 (PBS/Tween) and blocked with 200 μl of 1% bovine serum albumin in PBS (BSA/PBS) for 1 h at room temperature. After blocking, the plates were washed again and 50 μl of marmoset serum (diluted 1:5 in 1% BSA/PBS) added to each well and incubated overnight at 4° C. In addition, 50 μl of human IgE standards (doubling dilutions from 100 ng/ml to 1.56 ng/ml) were included on each plate. All assays were carried out in duplicate. Following overnight incubation, the plates were washed again and 50 μl of biotinylated mouse anti human IgE (2 μg/ml diluted in 1% BSA/PBS) added to each well and incubated at room temperature for 2 h. After 2 h the plates were washed again and 50 μl of streptavidin conjugated to horseradish peroxidase (diluted 1:1000 in 1% BSA/PBS) added to each well and incubated for 1 h at room temperature. The plates were washed one final time and developed with 100 μl TMB (0.1 mg/ml) containing 6 μl of hydrogen peroxide per 10 ml of TMB. The reaction was stopped by adding 20 μl of 2.5 M sulphuric acid, and the absorbance of each well was measured at 450 nm.

The specific IgG response was determined by coating a 96 well polystyrene plate with 50 μl of *N. americanus* ES products (5 μg/ml in 0.05 M sodium carbonate/bicarbonate buffer, pH 9.6) and incubating at 4° C. overnight. The plate was washed with PBS/Tween and the wells blocked with 200 μl of 5% skimmed milk powder/PBS for 1 hr at 37° C. The plate was washed as before and 50 μl of marmoset serum, diluted 1:100 in skimmed milk powder/PBS added to individual wells and the plate incubated at 4° C. overnight. The plate was washed again and 50 μl of sheep anti human IgG (The Binding Site, Inc., San Diego, Calif.) diluted 1:1000 in blocking agent was added to individual wells and the plate incubated for 2 h at room temperature. The plates were washed again, and antibody binding visualised by the addition of 100 µl of TMB prepared as described above. The reaction was stopped by adding 20 µl of 2.5 M sulphuric acid, and the absorbance of each well was measured at 450 nm. All assays were carried out in duplicate. ELISA values are expressed as the absorbance at 450 nm after the subtraction of a negative control.

Sera from infected marmosets were also analysed by Western blotting. *N. americanus* ES products (10 µg/lane) were separated, under reducing conditions, by 12% SDS-PAGE (Laemmli, U. K. *Nature* 227: 680–685 (1970)) and transferred onto a nitrocellulose membrane (Towbin, H., Staehelin, T. and Gordon, J. *Proceedings of the National Academy of Science* 76(9): 4350–4354 (1979)). Western blots were blocked for 1 h in 5% skimmed milk powder in TBS at room temperature. Marmoset serum (diluted 1:200 in 5% skimmed milk powder/TBS) was added to the blots and incubated overnight at 4° C. Blots were washed with TBS/0.05% Tween 20 and then incubated in sheep anti-human IgG (The Binding Site, Inc.) diluted 1:1000 in 5% skimmed milk powder/TBS for 2 h at room temperature. Following washing, blots were developed in chloronapthol (10 mg/ml) containing 30 µl of hydrogen peroxide.

Furthermore, whole blood basophils collected from the animals were challenged for their ability to release histamine. One hundred (100) µl of whole blood was collected from the primates into heparinized tubes and the volume was made up to 500 µl using PIPES buffer (0.01 M Piperazine-N'N-bis[2-ethaneculfonic acid], 0.14 M sodium acetate, 5 mM potassium acetate, 0.1% glucose, 1 mM $CaCl_2$ and 0.03% human serum albumin, pH 7.4). Spontaneous histamine release was assessed following incubation for 1 h at 37° C., while total histamine release was assessed when 50 µl of whole blood in 450 µl $dH_2O$ was freeze-thawed three times. Standard histamine calibrators of 0, 10, 25, 50, 100 and 250 ng/ml (Hycor Biomedical Ltd., Penicuik, UK) were included with each set of whole blood challenges, mediated by anti-IgE, ES products or recombinant calreticulin. Histamine released in each whole blood challenge was detected using a Histamine Assay Kit (Hycor Biomedical Ltd.). Fifty (50) µl of challenged whole blood was added to histamine-coated 96 wells followed by 50 µl of mouse anti-histamine monoclonal conjugated to alkaline phosphatase. Following an incubation of 1 h at room temperature, wells were washed three times with a provided EIA wash solution. Antibody binding was visualised by the addition of 100 µl of 1 mg/ml of p-nitrophenyl phosphate (pNPP) substrate The plates were developed for 1 h at 37° C. and the absorbance measured at 405 nm using a Dynex MRX absorbance microplate reader (DYNEX Technologies, Chantilly, Va.). For all samples and calibrators the percentage binding was determined by the following:

$$\text{Percentage Binding} = 100 \times \frac{\text{Absorbance of Sample}}{\text{Average Absorbance of Zero Calibrator}}$$

A standard curve was constructed by plotting the Percentage Binding against concentration for each histamine calibrator, and the levels of histamine in each challenge were determined from this curve.

Results

Figure 2:
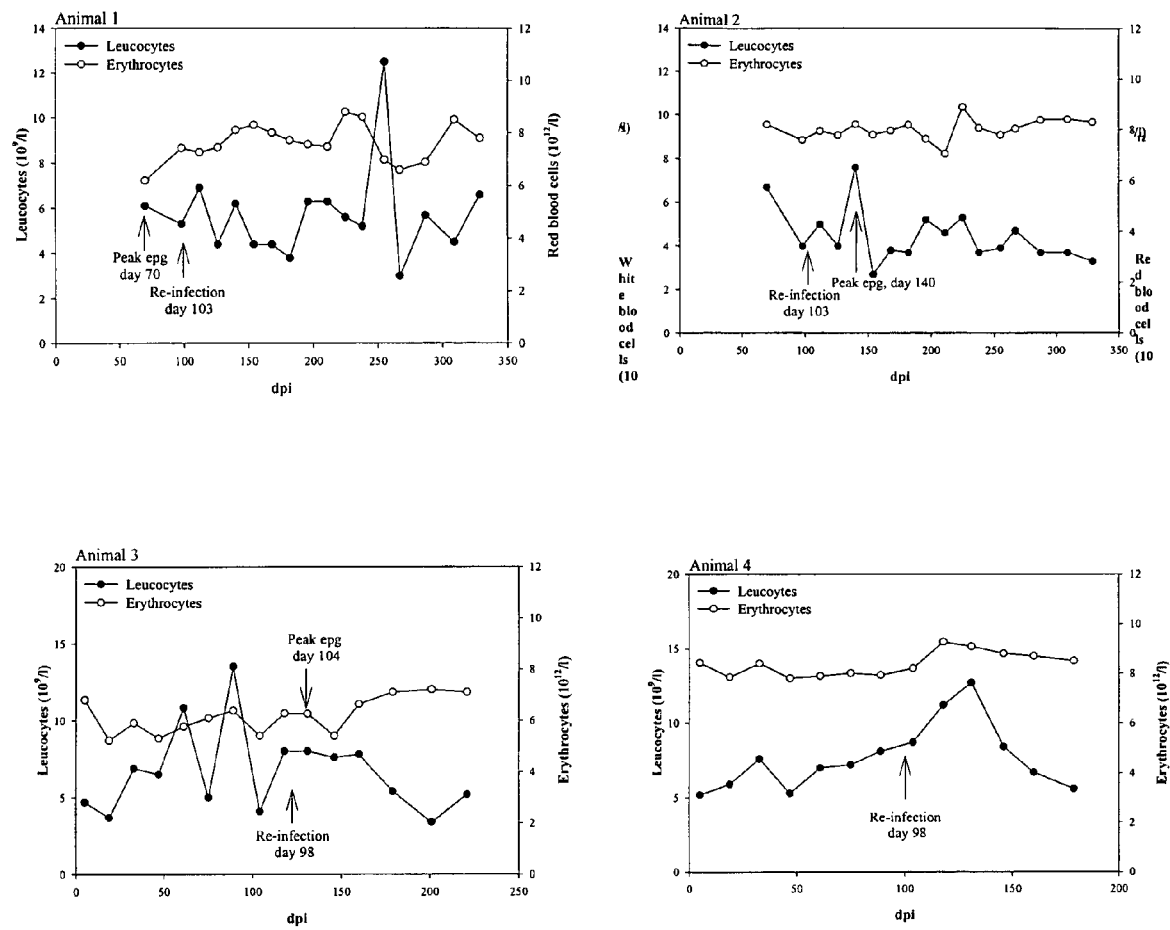
FIG. 2 are the plots showing the change in peripheral blood leucocytes and erythrocytes along the time course of infection in Primates 1–4.
Figure 3:
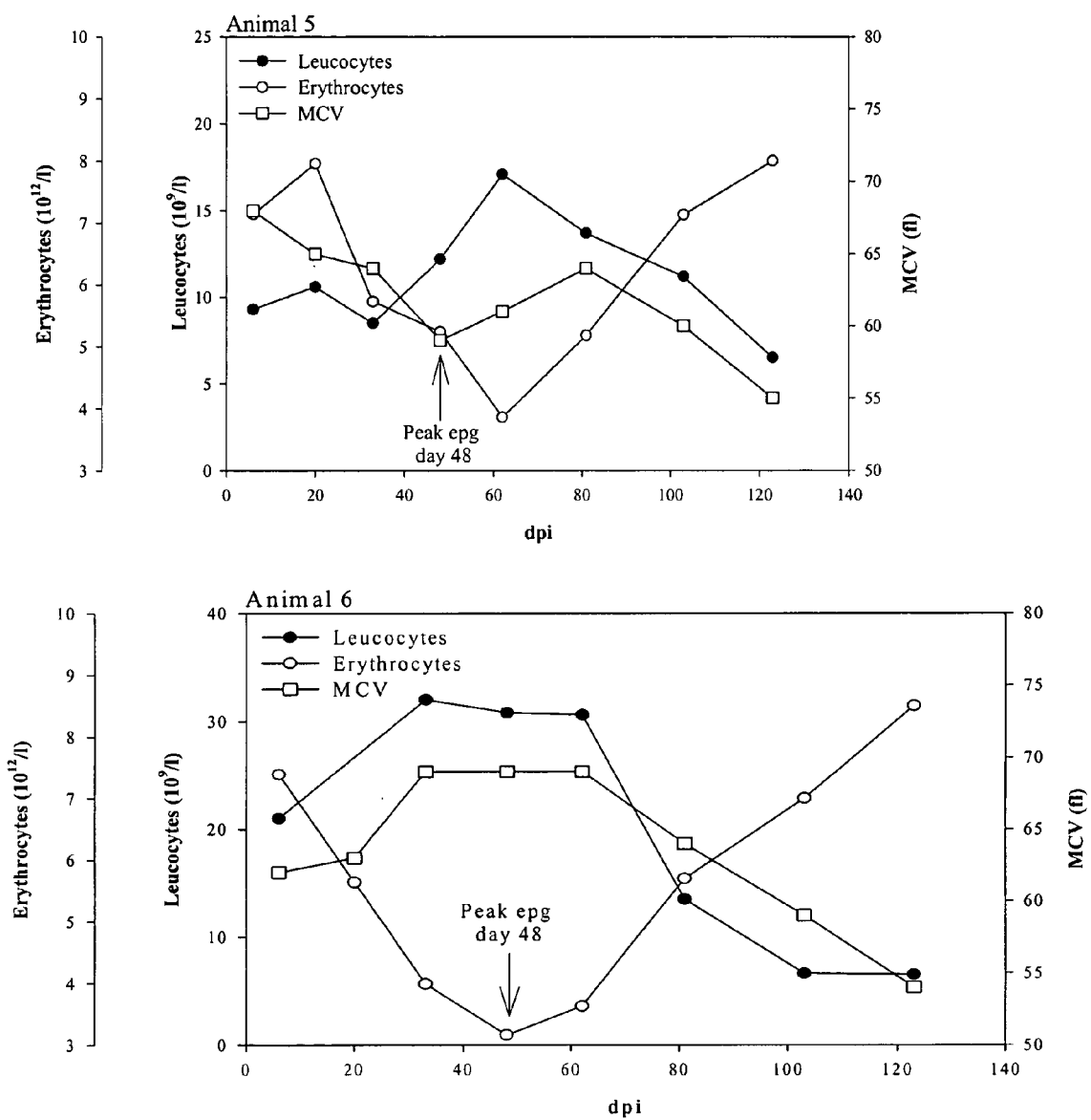
FIG. 3 are the plots showing the change in peripheral blood leucocytes, erythrocytes and mean erythrocyte cell volume along the time course of infection in Animals 5 and 6.

FIG. 1 shows the egg production, haemoglobin levels and packed cell volume of each different primate over time. FIG. 2 shows the change in peripheral blood leucocytes and erythrocytes along the time course of infection in Primates 1–4. FIG. 3 shows the change in peripheral blood leucocytes, erythrocytes and mean erythrocyte cell volume along the time course of infection in Animals 5 and 6.

Figure 4:
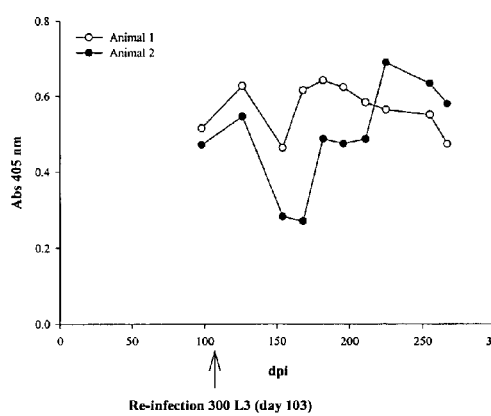
FIG. 4 are the plots showing the results from ELISA (Panels A–C) and a Western blot (Panel D) showing analysis of the antigenicity of the ES products of *N. americanus* probed with post-infection marmoset plasma followed by anti-human IgG.
Figure 4:
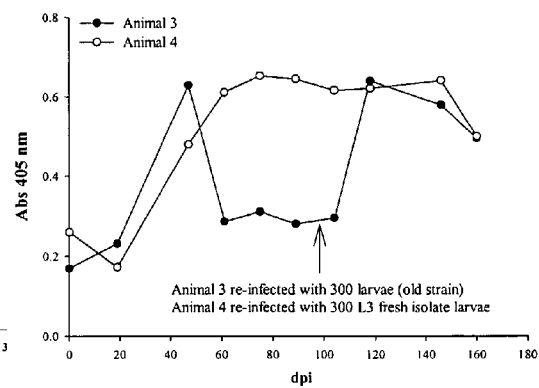
Figure 4:
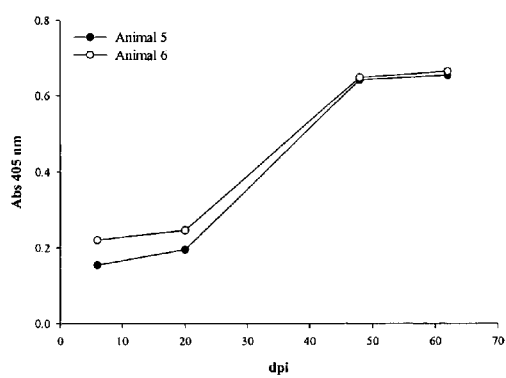
Figure 4:
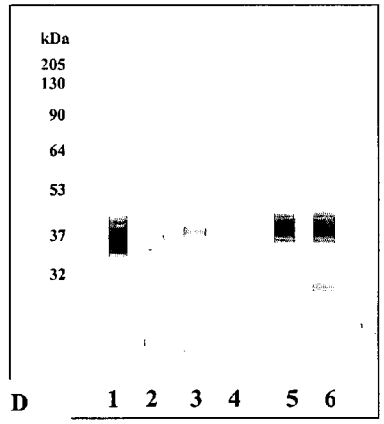

FIG. 4 shows, in panels A–C, the results from ELISA, and, in panel D, Western blot analysis of the antigenicity of the ES products of *N. americanus* probed with post-infection marmoset plasma followed by anti-human IgG. The Western blot analyses were carried out on the days of peak antigenicity. For comparison, the peak day of antigenicity as assessed by band intensity on Western blot and peak egg output are indicated below.

TABLE 1

Lanes of the Western blot shown in FIG. 4, panel D.

| Lane 1 | Animal 1 | Peak antigenicity day 70–84 | Peak eggs per gram of fecal matter (epg) day 70–112. |
| Lane 2 | Animal 2 | Peak antigenicity day 70 | Peak epg day 84/140. |
| Lane 3 | Animal 3 | Peak antigenicity day 75 | Peak epg day 47–61. |
| Lane 4 | Animal 4 | Peak antigenicity not applicable | Peak epg NA. |
| Lane 5 | Animal 5 | Peak antigenicity day 33–123 | Peak epg day 48–103 |
| Lane 6 | Animal 6 | Peak antigenicity day 33–123 | Peak epg day 48–81 |

Figure 5:
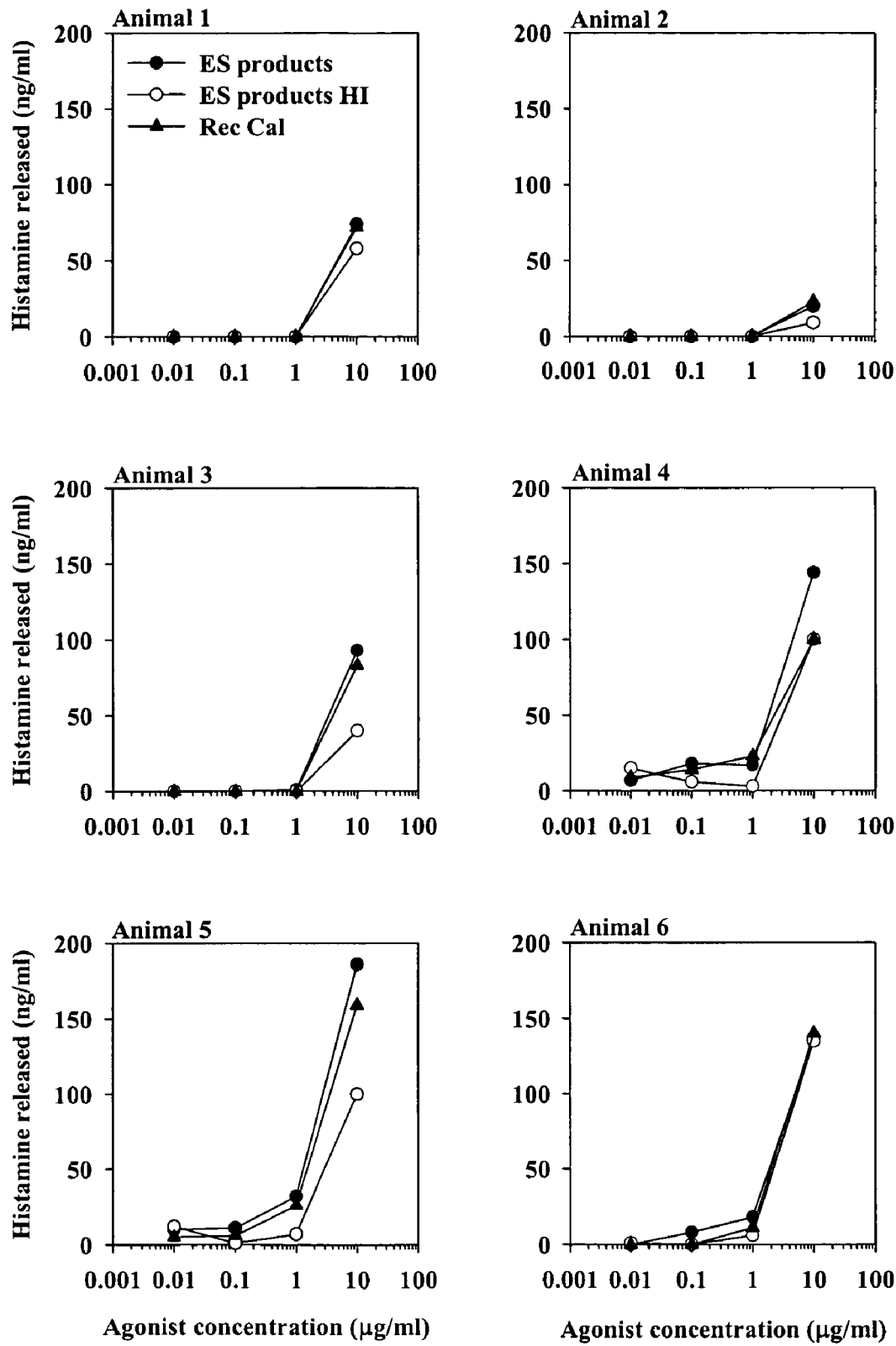
FIG. 5 are the plots showing basophil histamine release in infected animals following challenge with *N. americanus* excretory/secretory (ES) products (intact or heat inactivated (HI) to neutralise enzymatic activity) and a recombinant hookworm allergen, calreticulin (recCAL). Histamine release was measured using a Histamine Assay Kit (Hycor Biomedical Ltd.) as described.
Figure 6:
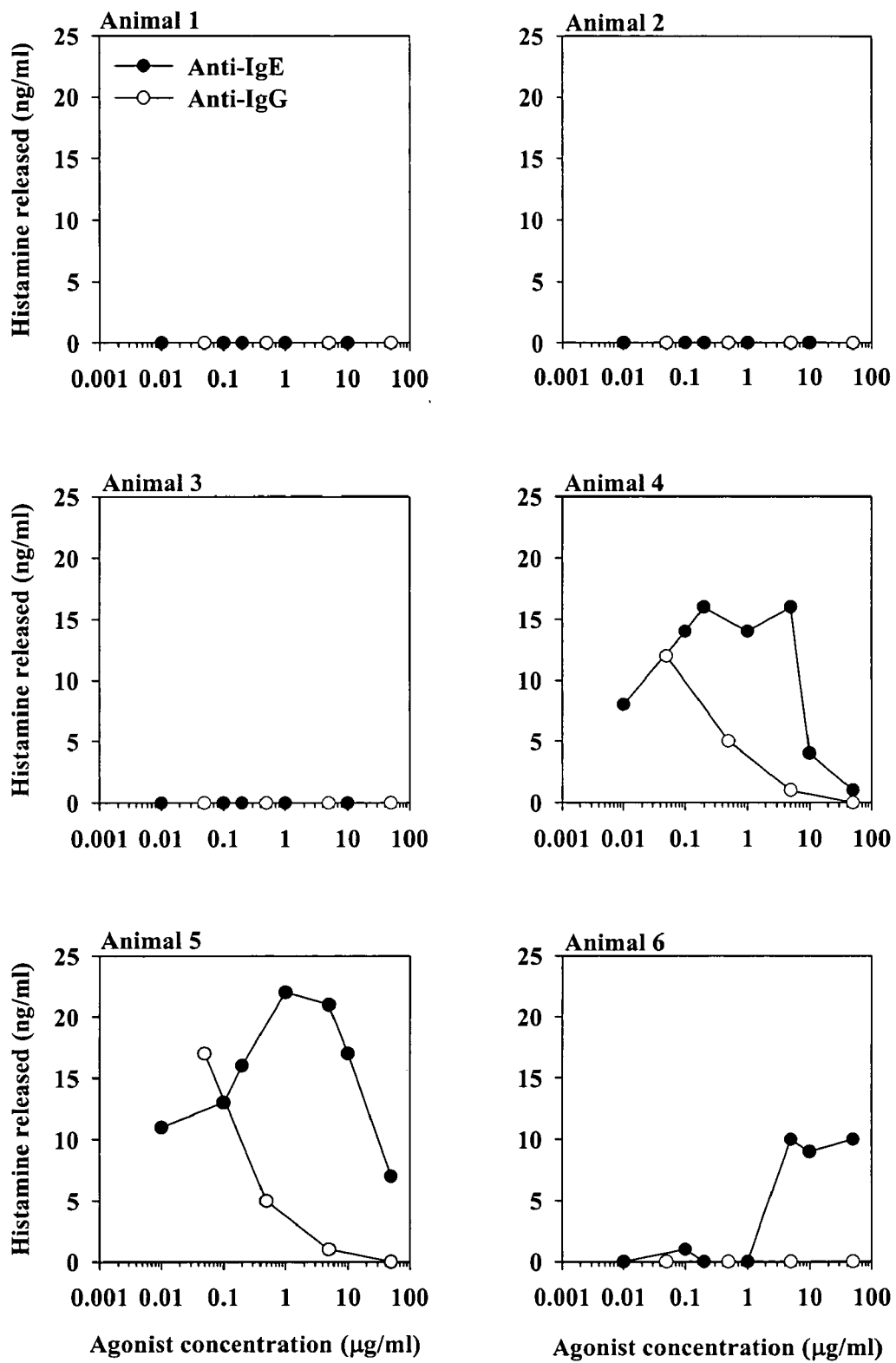
FIG. 6 are the plots showing basophil histamine release in infected animals following challenge with anti IgE, anti IgG. Histamine release was measured using a Histamine Assay Kit (Hycor Biomedical Ltd.) as described.

FIGS. 5 and 6 show basophil histamine release in infected animals following challenge with anti IgE, anti IgG, *N. americanus* excretory/secretory (ES) products (intact or heat inactivated (HI) to neutralise enzymatic activity) and a recombinant hookworm allergen, calreticulin (recCAL). Histamine release was measured using was detected using a Histamine Assay Kit (Hycor Biomedical Ltd.) as described in the materials and methods.

These results demonstrate that five from the six animals exposed to hookworm larvae demonstrated evidence of infection as indicated by the appearance of eggs in faeces (FIG. 1). These results also demonstrate that all the animals reacted to infection immunologically, yet only animals exposed to the recently acquired field isolate demonstrated infection-associated pathology, with a dramatic reduction in haemoglobin (Hb) and packed cell volume (PCV) 48–62 days post infection. It is possible that Animal 4 (FIG. 1, panel B) was protected against infection by the new field isolate by prior infection to what appears to be an attenuated laboratory strain. The dramatic fall in haemoglobin and PCV levels, accompanied by evidence of a microcytic anaemia, presumably as a direct result of blood loss in the lungs during transit by infective larvae, and feeding by adult worms in the gut (Girod, N., Brown, A. P., Billett, E. E. and Pritchard, D. I. *International/Journal for Parasitology*, 33(1):71–80(2003)) in Animals 5 and 6, when compared to Animals 1–4, likely indicates that the hamster adapted laboratory strain had become attenuated and was, therefore, no longer able to exhibit the full pathology of the infection in the primates. This is reflected by the fact that the *Necator* adult secretions from the adapted strain have lost the ability to inhibit human platelet aggregation, as demonstrated according to Furmidge B. A. et al., *Parasitology* 112 81–87 (1995).

The results shown in FIGS. 2 and 3 demonstrate that the erythrocyte numbers in Animals 5 and 6 were reduced during infection, reaching their lowest levels 40–60 days post-infection, corresponding to peak egg output (FIG. 3), but no such similar result was seen with Animals 1–4 (FIG.

2). Similarly, leukocyte numbers in Animals 5 and 6 were seen to increase during infection with the new field isolate, but, again, no such increase was observed in Animals 1–4 (FIG. 2). However, interestingly, Animal 4, when re-infected with the new field isolate, showed an increase in leukocyte numbers following re-infection (FIG. 2, panel B). It was also noticeable that Animal 5, exposed to the new field isolate alone, in addition to showing evidence of pathology as assessed by PCV and haemoglobin levels, also exhibited evidence of microcytic anaemia, in that infection with the new isolate had a significant effect on the mean erythrocyte cell volume (FIG. 3).

In all cases the antigenicity of infection was confirmed by the appearance of specific IgG antibodies in ELISA to *N. americanus* ES products (FIG. 4, Panels A–C). Antibodies recognised the classical hookworm 33 kDa antigen (as described in Carr, A. and Pritchard, D. I., *Parasite Immunology* 9 219–234 (1987)) on Western blots (FIG. 4, Panel D). Although the response was stronger in some individuals than others, the peak response on Western blots corresponded in most cases with peak egg output.

As a result of the characteristic elevation of total IgE levels by hookworm infection, the sensitisation of basophiles with hookworm specific IgE was also investigated. It can be seen from FIG. 5 that 5 out of 6 animals demonstrated significant histamine release to ES products and a recombinant hookworm allergen calreticulin. To control for the possible non-specific release of histamine by enzymes in ES products (Phillips C., et al., *Journal of Leukocyte Biology*, 73(1):165–71 (2003)) some preparations were heat inactivated by boiling for 30 minutes to neutralise activity (untreated ES released 2439±66.1 fluorescence units over 2 h, no activity was detected in heat inactivated ES products). Significantly, heat inactivated ES products produced a similar level of release, indicating the presence of allergenic material in ES products. To control for the ability of basophiles to release histamine, cells were also challenged with anti IgG and anti IgE (FIG. 6). Three (3) out of the six animals exposed to hookworm released histamine to anti IgE to a greater extent than that induced by anti IgG. The failure of Animals 1, 2 and 4 to release histamine suggested that the cells were not sufficiently sensitised with hookworm-specific IgE (Animals 1, 2 and 4 showed the lowest levels of plasma IgE), or that a degree of receptor blockade was operating.

In addition, the pathology of the infected animals was also investigated. An autopsy was conducted on each of the animals (333 days post-infection, Animals 1 and 2; 235 days, Animals 3 and 4; and 137, Animals 5 and 6). The small intestines were removed from each animal, opened along their length and placed in Hanks saline at 37° C. to allow any remaining worms to detach. No residual worms were observed in Animals 1–4, nine worms were observed in Animal 5—these consisted of 4 males, 2 females, and 3 worms which were fixed 'in situ' for histology and unable to be accurately sexed. Eleven (11) worms were observed in Animal 6, comprising 5 males, 2 females, and 4 worms of undetermined sex fixed 'in situ'.

All publications cited herein are hereby incorporated by reference in their entirety, unless otherwise indicated.

The foregoing discloses preferred embodiments of the present invention, and numerous modifications or alterations may be made without departing from the spirit and the scope of the invention.

What is claimed is:

1. A method of maintaining human hookworm in a marmoset, comprising:
   a. administering a non-adapted human hookworm to the marmoset to produce a human hookworm infection therein, and
   b. maintaining the hookworm-infected marmoset.

2. The method of claim 1, wherein the non-adapted human hookworm is a fresh human hookworm isolate.

3. The method of claim 1, wherein the human hookworm is *Necator americanus*.

4. The method of claim 1, wherein the marmoset is *Callithrix jacchus*.

5. The method of claim 1, wherein the marmoset is infected with from about 100 to about 1000 larvae.

6. The method of claim 1, wherein the human hookworm infection in the marmoset exhibits at least one of a patency, pathology, or immunology substantially similar to a hookworm infection in a human.

7. A human hookworm model comprising a marmoset infected with a human hookworm.

8. The model of claim 7, wherein a human hookworm infection is maintained in the marmoset.

9. A method of producing a human hookworm, comprising:
   a. administering a nan-adapted human hookworm to a marmoset to produce a human hookworm infection in the marmoset,
   b. maintaining the hookworm-infected marmoset,
   c. obtaining a fecal material from the non-human hookworm-infected marmoset, and
   d. isolating the human hookworm from the fecal material of the non-human hookworm-infected marmoset.

* * * * *